US008236884B2

(12) United States Patent
Smith et al.

(10) Patent No.: US 8,236,884 B2
(45) Date of Patent: *Aug. 7, 2012

(54) HIGH PERMEABILITY SUPERABSORBENT POLYMER COMPOSITIONS

(75) Inventors: Scott J. Smith, Greesnboro, NC (US); Stan McIntosh, Greensboro, NC (US); David L. Bergman, Jr., Greensboro, NC (US)

(73) Assignee: Evonik Stockhausen, LLC, Greensboro, NC (US)

( * ) Notice: Subject to any disclaimer, the term of this patent is extended or adjusted under 35 U.S.C. 154(b) by 802 days.

This patent is subject to a terminal disclaimer.

(21) Appl. No.: 11/690,611

(22) Filed: Mar. 23, 2007

(65) Prior Publication Data

US 2008/0234420 A1    Sep. 25, 2008

(51) Int. Cl.
*C08K 3/32* (2006.01)

(52) U.S. Cl. ........ 524/405; 524/401; 524/407; 524/415; 524/419; 523/200; 423/281

(58) Field of Classification Search .................. 524/405, 524/401, 407, 415, 419; 523/200; 423/281
See application file for complete search history.

(56) References Cited

U.S. PATENT DOCUMENTS

| | | | |
|---|---|---|---|
| 4,587,308 A * | 5/1986 | Makita et al. ................. 525/373 |
| 4,771,105 A | 9/1988 | Shirai et al. |
| 5,451,613 A | 9/1995 | Smith et al. |
| 5,462,972 A | 10/1995 | Smith et al. |
| 5,562,646 A | 10/1996 | Goldman et al. |
| 5,669,894 A | 9/1997 | Goldman et al. |
| 5,672,419 A * | 9/1997 | Mukaida et al. .............. 442/364 |
| 5,849,405 A | 12/1998 | Wang et al. |
| 5,985,432 A | 11/1999 | Wang et al. |
| 6,011,196 A | 1/2000 | Wang et al. |
| 6,099,950 A * | 8/2000 | Wang et al. ................. 428/304.4 |
| 6,121,509 A | 9/2000 | Ashraf et al. |
| 6,229,062 B1 | 5/2001 | Mandell et al. |
| 6,297,335 B1 | 10/2001 | Funk et al. |
| 6,414,214 B1 | 7/2002 | Engelhardt et al. |
| 6,603,055 B2 | 8/2003 | Mitchell et al. |
| 6,623,576 B2 | 9/2003 | Mitchell et al. |
| 6,831,122 B2 * | 12/2004 | Daniel et al. .................. 524/417 |
| 6,906,131 B2 | 6/2005 | Ahmed et al. |
| 7,163,969 B2 | 1/2007 | Ahmed et al. |

(Continued)

FOREIGN PATENT DOCUMENTS

CA    2460152 A1    3/2003

(Continued)

OTHER PUBLICATIONS

Invitation to Pay Additional Fees and, Where Applicable, Protest Fee, mailed on Jun. 5, 2008 in PCT/US2007/089033.

(Continued)

*Primary Examiner* — Peter D. Mulcahy
*Assistant Examiner* — Henry Hu
(74) *Attorney, Agent, or Firm* — Smith Moore Leatherwood LLP; Philip P. McCann

(57) ABSTRACT

The invention relates to absorptive, crosslinked polymeric composition that are based on partly neutralized, monoethylenically unsaturated monomer carrying acid groups wherein the absorptive crosslinked polymer may be coated with a polymeric coating, and have improved properties, in particular in respect of their capacity for transportation of liquids in the swollen state, and which have a high capacity and a high gel bed permeability.

11 Claims, 4 Drawing Sheets

U.S. PATENT DOCUMENTS

| | | | |
|---|---|---|---|
| 7,169,843 B2 | 1/2007 | Smith et al. | |
| 7,173,086 B2 | 2/2007 | Smith et al. | |
| 7,241,820 B2 | 7/2007 | Smith et al. | |
| 7,291,674 B2 | 11/2007 | Kang et al. | |
| 7,312,286 B2 | 12/2007 | Lang et al. | |
| 7,335,713 B2 | 2/2008 | Lang et al. | |
| 7,399,813 B2 | 7/2008 | Lang et al. | |
| 7,427,650 B2 | 9/2008 | Smith et al. | |
| 7,482,058 B2 | 1/2009 | Ahmed et al. | |
| 7,488,541 B2 | 2/2009 | Ahmed et al. | |
| 7,579,402 B2 | 8/2009 | Ahmed et al. | |
| 7,816,426 B2 * | 10/2010 | Ahmed et al. | 523/200 |
| 2002/0128618 A1 | 9/2002 | Frenz et al. | |
| 2003/0125684 A1 | 7/2003 | Qin | |
| 2003/0157857 A1 * | 8/2003 | Cook et al. | 442/327 |
| 2003/0219594 A1 | 11/2003 | Qin et al. | |
| 2004/0077796 A1 | 4/2004 | Daniel et al. | |
| 2004/0214946 A1 | 10/2004 | Smith et al. | |
| 2005/0013992 A1 | 1/2005 | Azad et al. | |
| 2005/0027268 A1 | 2/2005 | Qin et al. | |
| 2005/0096435 A1 | 5/2005 | Smith et al. | |
| 2005/0245684 A1 | 11/2005 | Daniel et al. | |
| 2006/0025030 A1 | 2/2006 | Funk et al. | |
| 2006/0173431 A1 | 8/2006 | Laumer et al. | |
| 2006/0173432 A1 | 8/2006 | Laumer et al. | |
| 2006/0173433 A1 | 8/2006 | Laumer et al. | |
| 2007/0066718 A1 | 3/2007 | Smith et al. | |
| 2007/0066754 A1 | 3/2007 | Loeker et al. | |
| 2007/0135554 A1 * | 6/2007 | McIntosh et al. | 524/492 |
| 2007/0167560 A1 | 7/2007 | Smith et al. | |
| 2007/0244283 A1 * | 10/2007 | Riegel et al. | 526/318 |
| 2008/0009616 A1 | 1/2008 | Frank et al. | |
| 2008/0021130 A1 * | 1/2008 | McIntosh et al. | 523/111 |
| 2009/0023848 A1 | 1/2009 | Ahmed et al. | |
| 2009/0134357 A1 | 5/2009 | Bub et al. | |
| 2009/0191408 A1 | 7/2009 | Tian et al. | |

FOREIGN PATENT DOCUMENTS

| | | |
|---|---|---|
| CN | 02819951.0 | 8/2007 |
| EP | 1438354 A1 | 7/2004 |
| JP | 9124879 | 5/1997 |
| JP | 2004097255 | 4/2004 |
| WO | 9925745 | 5/1999 |
| WO | 0046260 | 8/2000 |
| WO | 0055245 | 9/2000 |
| WO | 03104543 | 12/2003 |
| WO | 2004018005 | 3/2004 |
| WO | 2004024816 | 3/2004 |
| WO | 2005094749 | 10/2005 |
| WO | 2005097881 | 10/2005 |
| WO | 2006082188 | 8/2006 |
| WO | 2006082189 | 8/2006 |
| WO | 2006082197 | 8/2006 |
| WO | 2007070262 A2 | 6/2007 |
| WO | 2007070776 A2 | 6/2007 |

OTHER PUBLICATIONS

U.S. Appl. No. 12/254,434, filed Oct. 20, 2008, Azad et al.
U.S. Appl. No. 12/256,038, filed Oct. 22, 2008, Tian et al.
U.S. Appl. No. 12/277,637, filed Nov. 25, 2008, Tian et al.
U.S. Appl. No. 12/516,745, filed Dec. 18, 2007, Loeker et al.
Unpublished pending U.S. Appl. No. 11/301,359, filed Dec. 12, 2005 titled Thermoplastic Coated Superabsorbent Polymer Compositions.
Briggs, M.: "Boron Oxides, Boric Acid, and Borates" Kirk-Othmer Encyclopedia of Chemical Technology, vol. 4, 2001, pp. 259-283, XP002486769.
Database WPI Week 200425 Thomson Scientific, London, GB: AN 2004-263106 XP002486770 & JP-A-2004 097255.
Hu Z S et al.: "Study on antiwear and reducing friction additive of nanometer titanium borate" Wear Elsevier Science S. A., Lausanne, Switzerland, vol. 216, No. 1, (Mar. 15, 1998), pp. 87-91, XP002486768 NY USA.
International Search Report completed on Jul. 3, 2008 in PCT/US2007/089033.
Invitation to Pay Additional Fees and, Where Applicable, Protest Fee mailed on Jun. 5, 2008 in PCT/US2007/089033.
Written Opinion of the International Searching Authority mailed on Jul. 21, 2008 in PCT/US2007/089033.

* cited by examiner

HIGH PERMEABILITY SUPERABSORBENT POLYMER COMPOSITIONS

BACKGROUND

A superabsorbent material in general refers to a water-swellable, water-insoluble, material capable of absorbing at least about 10 times its weight, and up to about 30 times or more its weight in an aqueous solution containing 0.9 weight percent sodium chloride solution in water. The present invention relates to superabsorbent polymer compositions, which absorb water, aqueous liquids, and blood.

A superabsorbent polymer is a crosslinked partially neutralized polymer that is capable of absorbing large amounts of aqueous liquids and body fluids, such as urine or blood, with swelling and the formation of hydrogels, and of retaining them under a certain pressure in accordance with the general definition of superabsorbent material. Superabsorbent polymer compositions may include post-treatment of the superabsorbent polymer such as surface crosslinking, surface treatment, and other treatment. Superabsorbent polymer particles are particles of superabsorbent polymers or superabsorbent polymer compositions. The acronym SAP may be used in place of superabsorbent polymer, superabsorbent polymer composition, and particles herein. A comprehensive survey of superabsorbent polymers, and their use and manufacture, is given in F. L. Buchholz and A. T. Graham (editors) in "Modern Superabsorbent Polymer Technology," Wiley-VCH, New York, 1998.

Commercially available superabsorbent polymer compositions include crosslinked polyacrylic acids or crosslinked starch-acrylic acid graft polymers, in which some of the carboxyl groups are neutralized with sodium hydroxide solution or potassium hydroxide solution. A primary use of superabsorbent polymer compositions is in sanitary articles, such as babies' diapers, incontinence products, or sanitary towels. For fit, comfort, and aesthetic reasons, and from environmental aspects, there is an increasing trend to make sanitary articles smaller and thinner. This is being accomplished by reducing the content of the high volume fluff fiber in these articles. To ensure a constant total retention capacity of body fluids in the sanitary articles, more superabsorbent polymer content is being used in these sanitary articles.

Permeability is a measure of the effective connectedness of a porous structure, be it a mat of fiber, or a slab of foam or, in this case, crosslinked polymers, and may be specified in terms of the void fraction, and extent of connectedness of the superabsorbent polymer composition. Gel permeability is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage).

One method to increase permeabilities in extremely thin diapers with low fiber content is to increase the amount of crosslinking of the superabsorbent polymer composition. However, the absorption and retention values of the superabsorbent polymer compositions are reduced to undesirably low levels when the crosslinking of the superabsorbent polymer is increased.

It is an object of the present invention to provide superabsorbent polymer compositions possessing improved application properties including a high absorption capacity to retain fluids under no load, high absorption capacities to retain fluid under pressure, and improved gel bed permeability.

SUMMARY

An embodiment of the present invention comprises at least a high permeability superabsorbent polymer composition comprising superabsorbent polymer particles surface-treated with from about 0.01% to about 2% by weight of an inorganic metal compound, based on the dry superabsorbent polymer composition, wherein the superabsorbent polymer composition exhibits a Centrifuge Retention Capacity of at least about 30 g/g and a free swell gel bed permeability of at least 10 Darcy as measured by the Free Swell Gel Bed Permeability Test.

In addition, another embodiment of the present invention comprises a process of treating superabsorbent polymer particles with finely-divided, water-insoluble inorganic metal salt comprising the steps of a) providing superabsorbent polymer particles; b) preparing a first solution of a first inorganic metal salt; c) adding to and mixing with the first solution of b) a second solution of a second inorganic metal salt, wherein the first solution and second solution react on mixing to precipitate a third water-insoluble metal salt to form a water-insoluble metal salt slurry; d) optionally oxidizing the metal of the water-insoluble metal salt slurry to a higher valence state; and e) applying the water-insoluble metal salt slurry to a superabsorbent polymer particles without isolation and drying of the water-insoluble metal salt slurry.

In addition, another embodiment of the present invention comprises a process of treating superabsorbent polymer particles with finely-divided, water-insoluble inorganic metal salt comprising the steps of a) providing superabsorbent polymer particles; b) preparing a first solution of a first inorganic metal salt; c) preparing a second solution of a second inorganic metal salt; d) applying the first solution and second solution to the superabsorbent polymer particles to form a water-insoluble inorganic metal salt precipitate directly on or in the vicinity of the surface of the superabsorbent polymer particles.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

In addition, the present invention is directed to absorbent compositions or sanitary articles that may contain superabsorbent polymer compositions of the present invention.

FIGURES

The foregoing and other features, aspects, and advantages of the present invention will become better understood with regard to the following description, appended claims, and accompanying drawings where:

DEFINITIONS

Figure 1:
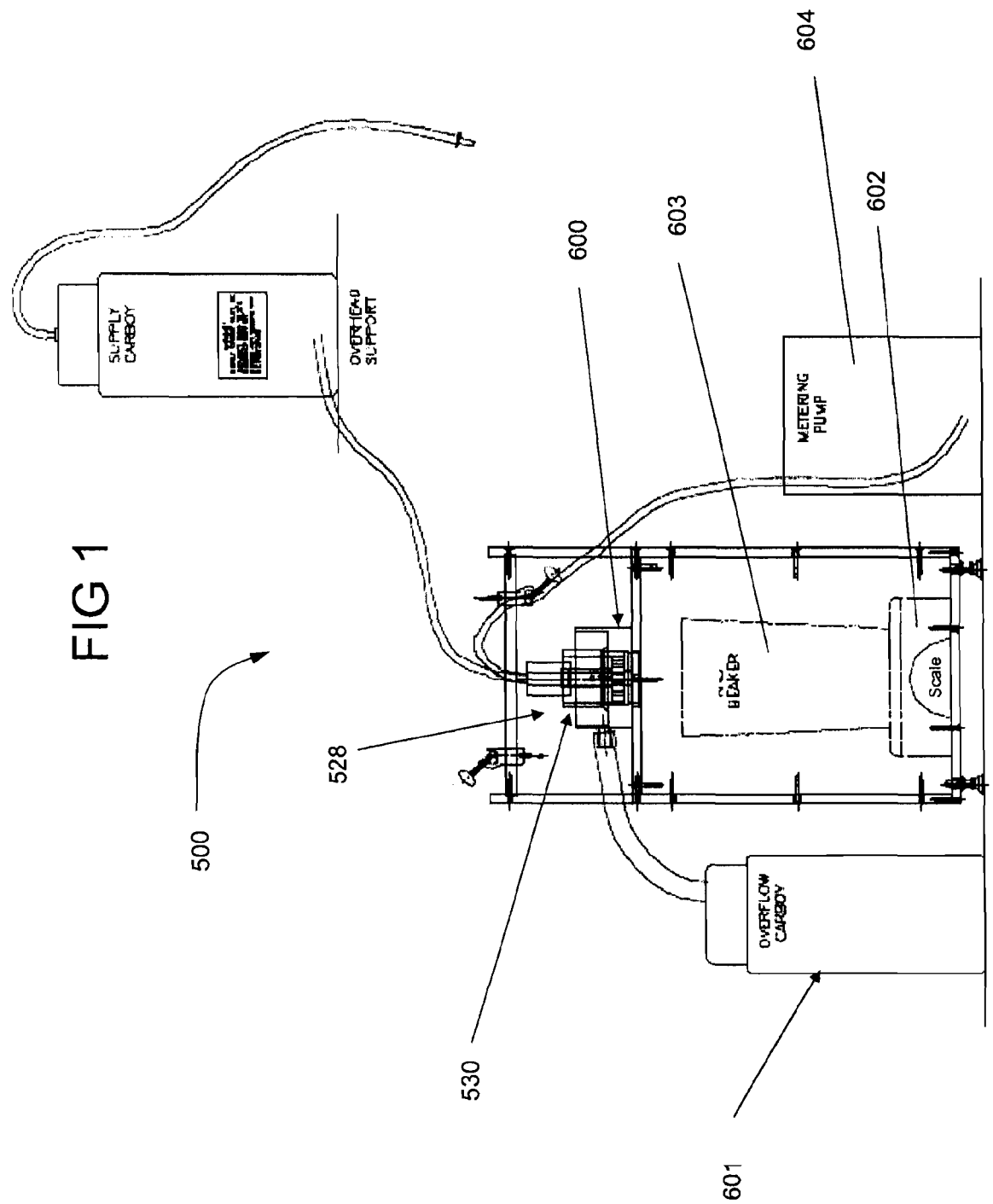
FIG. 1 is a side view of the test apparatus employed for the Free Swell Gel Bed Permeability Test.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices that can absorb and contain fluids. For example, personal care absorbent articles refer to devices that are placed against or near the skin to absorb and contain the various fluids discharged from the body.

The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "crosslinked" used in reference to the superabsorbent polymer refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "dry superabsorbent polymer composition" generally refers to the superabsorbent polymer composition having less than about 10% moisture.

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod-like, polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "superabsorbent materials" refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" refers to a superabsorbent polymer comprising a surface additive in accordance with the present invention.

The terms "superabsorbent polymer" and "superabsorbent polymer preproduct" refer to a material that is produced by conducting all of the steps for making a superabsorbent polymer as described herein, up to and including drying the material, and coarse grinding in a crusher.

The term "preproduct fines" refers to a material that is produced by conducting all of the steps for making a superabsorbent polymer as described herein, up to and including drying the material, and coarse grinding in a crusher, and removing particles greater than about 150 microns.

The term "surface crosslinking" means that the level of functional crosslinks in the vicinity of the surface of the superabsorbent polymer particle generally is higher than the level of functional crosslinks in the interior of the superabsorbent polymer particle. As used herein, "surface" describes the outer-facing boundaries of the particle. For porous superabsorbent polymer particles, exposed internal surface also are included in the definition of surface.

The term "thermoplastic" describes a material that softens when exposed to heat and which substantially returns to a non-softened condition when cooled to room temperature.

The term "% by weight" or "% wt" when used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

An embodiment of the present invention includes a high-capacity superabsorbent polymer composition comprising superabsorbent polymer particles surface treated with from about 0.01% to about 2% by weight of an inorganic metal compound, based on the dry superabsorbent polymer composition wherein the superabsorbent polymer composition exhibits a Centrifuge Retention Capacity of at least about 30 g/g and a free swell gel bed permeability of at least 10 Darcy as measured by the Free Swell Gel Bed Permeability.

Another embodiment of the present invention includes a high-capacity superabsorbent polymer composition comprising a superabsorbent polymer comprising:

a) from about 55% to about 99.9% by weight of the superabsorbent polymer of polymerizable unsaturated acid group containing monomers based on the superabsorbent polymer; and b) from about 0.001% to about 5% by weight of internal crosslinking agent based on the polymerizable unsaturated acid group containing monomer, wherein the superabsorbent polymer has a degree of neutralization of greater than about 25%, wherein elements a) and b) are polymerized and prepared into superabsorbent polymer particles further comprising the following surface additives to form surface-treated superabsorbent polymer particles i) from about 0.001% to about 5% by weight of surface crosslinking agent based on the superabsorbent polymer composition;

ii) from about 0.01% to about 2% by weight of a water-insoluble inorganic metal compound based on the superabsorbent polymer composition; and iii) from 0% to about 5% by weight of a polymeric coating based on the superabsorbent polymer composition Another embodiment of the present invention comprises a process of treating superabsorbent polymer particles with finely-divided, water-insoluble inorganic metal salt comprising the steps of a) supplying superabsorbent polymer particles; b) preparing a first solution of a first inorganic metal salt; c) adding to and mixing with the first solution of b) a second solution of a second inorganic metal salt, wherein the first solution and second solution react on mixing to precipitate a third water-insoluble metal salt to form a water-insoluble metal salt slurry; d) optionally oxidizing the metal of the water-insoluble metal salt slurry to a higher valence state; and e) applying the water-insoluble metal salt slurry to a superabsorbent polymer particles without isolation and drying of the water-insoluble metal salt slurry.

Another embodiment of the present invention comprises a process of treating superabsorbent polymer particles with finely-divided, water-insoluble inorganic metal salt comprising the steps of a) supplying superabsorbent polymer particles; b) preparing a first solution of a first inorganic metal salt; c) preparing a second solution of a second inorganic metal salt; d) applying the first solution and second solution to the superabsorbent polymer particles to form a water-insoluble inorganic metal salt precipitate directly on or in the vicinity of the surface of the superabsorbent polymer particles.

A superabsorbent polymer as set forth in embodiments of the present invention is obtained by the initial polymerization of from about 55% to about 99.9% by weight of the superabsorbent polymer of polymerizable unsaturated acid group containing monomer. A suitable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75% by weight of the acid groups to be carboxyl groups.

The acid groups are neutralized to the extent of at least about 25 mol %, that is, the acid groups are desirably present as sodium, potassium, or ammonium salts. In some aspects, the degree of neutralization may be at least about 50 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that can be copolymerized with the ethylenically unsaturated monomer may include, but is not limited to acrylamide, methacrylamide, hydroxyethyl acrylate, dimethylaminoalkyl(meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer of the invention also includes internal crosslinking agents. The internal crosslinking agent has at least two ethylenically unsaturated double bonds, or one ethylenically unsaturated double bond and one functional group that is reactive toward acid groups of the polymerizable unsaturated acid group containing monomer, or several functional groups that are reactive towards acid groups can be used as the internal crosslinking component and is desirably present during the polymerization of the polymerizable unsaturated acid group containing a monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri(meth)acrylates of butanediol or ethylene glycol, polyglycols or trimethylolpropane; di- and triacrylate esters of trimethylolpropane which may be oxyalkylated, desirably ethoxylated, with about 1 to about 30 moles of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl(meth)acrylate, alkoxylated allyl(meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived therefrom. Ionic crosslinkers such as multivalent metal salts may also be employed. Mixtures of the crosslinking agents mentioned can also be employed. The content of the internal crosslinking agents is from about 0.001% to about 5% by weight such as from about 0.2% to about 3% by weight based on the total amount of the polymerizable unsaturated acid group containing monomer.

In some aspects, initiators can be used for initiation of the free-radical polymerization. Suitable initiators include, but are not limited to, azo or peroxo compounds, redox systems or UV initiators, sensitizers, and/or radiation.

After polymerization, the superabsorbent polymer is generally formed into particles. The superabsorbent polymer particles may then be surface crosslinked after polymerization by the addition of a surface crosslinking agent and heat-treatment. In general, surface crosslinking is a process that is believed to increase the crosslink density of the polymer matrix in the vicinity of the superabsorbent particle surface with respect to the crosslinking density of the particle interior.

In some particular aspects, desirable surface crosslinking agents include chemicals with one or more functional groups that are reactive toward pendant groups of the polymer chains, typically the acid groups. The surface crosslinking agent may be present in an amount of from about 0.001% to about 5% by weight of the dry superabsorbent polymer composition, and such as from about 0.1% to about 3% by weight, and such as from about 0.1% to about 1% by weight, based on the weight of the dry superabsorbent polymer composition. Applicants have found that a heat treatment step after addition of the surface crosslinking agent is desirable.

In one particular aspect, the particulate superabsorbent polymer is coated or surface-treated with an alkylene carbonate followed by heating to effect surface crosslinking, which can improve the surface crosslinking density and the gel strength characteristics of the superabsorbent polymer particle. More specifically, the surface crosslinking agent is coated onto the superabsorbent polymer particulate by mixing the polymer particulate with an aqueous alcoholic solution of the alkylene carbonate surface crosslinking agent. The amount of alcohol is determined by the solubility of the alkylene carbonate and is kept as low as possible for various reasons. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer. In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, that may follow the coating treatment, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

While particles may be used by way of example of the physical form of superabsorbent polymer composition, the invention is not limited to this form and is applicable to other forms such as fibers, foams, films, beads, rods, and the like, as discussed above. In some aspects, when the superabsorbent polymer composition exists as particles or in granule form, it is desirable that these particles have a size of from about 150 μm to about 850 μm based on the sieving process that is well known in the superabsorbent industry.

In some aspects, the superabsorbent polymer composition of the present invention includes from 0% to about 5% by weight, and from about 0.001% to about 5% by weight, and from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, the Applicants have found that maleated polypropylene to be a desirable thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), poly(diallyldimethyl ammonium chloride). Poly(vinyl amines) include, but are not limited to, LUPAMIN® 9095 available from BASF Corporation, Mount Olive, N.J. Examples of natural-based cationic polymers include, but are not limited to, partially deacetylated chitin, chitosan, and chitosan salts. Synthetic polypeptides such as polyasparagins, polylysines, polyglutamines, and polyarginines are also suitable cationic polymers.

The superabsorbent polymer compositions according to the invention may include from about 0.01% to about 2% by weight, or from about 0.01% to about 1% by weight based on the dry superabsorbent polymer composition of a water-insoluble inorganic metal compound. The water-insoluble inorganic metal compound may include, but are not limited to, a cation selected from aluminum, titanium, calcium, or iron and an anion selected from phosphate, borate, or chromate. Examples of water-insoluble inorganic metal compounds include aluminum phosphate and an insoluble metal borate.

The insoluble metal borate is selected from titanium borate, aluminum borate, iron borate, magnesium borate, manganese borate, or calcium borate. The chemical formula TiBO will be used herein to designate titanium borate and analogous compounds such as titanium (III) borate $TiBO_3$. In addition, the chemical formulation also designates the case when titanium (III) borate $TiBO_3$ is treated with hydrogen peroxide to obtain titanium (IV) borate. The inorganic metal compound may have a mass median particle size of less than about 2 µm, and may have a mass median particle size of less than about 1 µm.

The inorganic metal compound can be applied in the dry physical form to the surface of the superabsorbent polymer particles. For this, the superabsorbent polymer particles can be intimately mixed with the finely divided inorganic metal compound. The finely divided inorganic metal compound is usually added at about room temperature to the superabsorbent polymer particles and mixed in until a homogeneous mixture is present. For this purpose, mixing is effected in suitable mixers known in the art, such as fluidized bed mixers, paddle mixers, rotary drum mixers, or twin-worm mixers. The mixing of the superabsorbent polymer particles with the finely divided water-insoluble inorganic metal compound may take place before or after any surface crosslinking, for example during the application of the surface crosslinking agent.

Alternatively, a suspension of a finely divided water-insoluble inorganic metal compounds can be prepared and applied to a particulate water absorbent polymer. The suspension is applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidals, viscosity modifiers, and other auxiliaries to assist in the preparation of the suspension. The suspension can be applied in conventional reaction mixers or mixing and drying systems as described above at a temperature in the range from room temperature to less than the boiling point of the dispersion medium, preferably at about room temperature. It is appropriate to combine the application of the suspension with a surface crosslinking step by dispersing the finely divided water-insoluble metal salt in the solution of the surface crosslinking agent. Alternatively, the suspension can also be applied before or after the surface crosslinking step. The application of the slurry may be followed by a drying step.

In some aspects, the superabsorbent polymer compositions according to the invention can include from 0% to about 5%, or in the alternative from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide is desirable. Products include SIPERNAT 22S and AEROSIL 200 available from Degussa Corporation, Parsippany, N.J. In some aspects, the particle diameter of the inorganic powder can be 1,000 µm or smaller, such as 100 µm or smaller.

In some aspects, the superabsorbent polymer compositions may also include from 0% to about 30% by weight of the dry superabsorbent polymer composition, such as from about 0.1% to about 5% by weight, of water-soluble polymers based by weight of the dry superabsorbent polymer composition, of partly or completely hydrolyzed polyvinyl acetate, polyvinylpyrrolidone, starch or starch derivatives, polyglycols, polyethylene oxides, polypropylene oxides, or polyacrylic acids.

In some aspects, additional surface additives may optionally be employed with the superabsorbent polymer particles, such as odor-binding substances, such as cyclodextrins, zeolites, inorganic or organic salts, and similar materials; anticaking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the superabsorbent polymer compositions of the present invention may be, after a heat treatment step, treated with water so that the superabsorbent polymer composition has a water content of up to about 10% by weight of the superabsorbent polymer composition. This water may be added with one or more of the surface additives from above added to the superabsorbent polymer.

The superabsorbent polymer compositions according to the invention are desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

The superabsorbent polymer particles of the present invention generally include particle sizes ranging from about 50 to about 1000 microns, or from about 150 to about 850 microns. The present invention may include at least about 40 wt % of the particles having a particle size from about 300 µm to about 600 µm, at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 microns, and less than about 30% by weight of particles having a size of less than about 300 microns as measured using for example a RO-TAP® Mechanical Sieve Shaker Model B available from W. S. Tyler, Inc., Mentor Ohio.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the organic solvent. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a superabsorbent preproduct. A superabsorbent pre-product as used herein is produced by repeating all of the steps for making the superabsorbent, up to and including drying the material, and coarse grinding in a crusher, and removing particles greater than about 850 microns and smaller than about 150 microns.

The superabsorbent polymer composition of the present invention exhibits certain characteristics, or properties, as measured by Free Swell Gel Bed Permeability (GBP), Centrifuge Retention Capacity (CRC), and absorbency under load at about 0.9 psi (AUL(0.9 psi)). The Free Swell Gel Bed Permeability (GBP) Test is a measurement of the permeability of a swollen bed of superabsorbent material in Darcy (e.g., separate from the absorbent structure) under a confining pressure after what is commonly referred to as "free swell" conditions. In this context, the term "free swell" means that the superabsorbent material is allowed to swell without a swell restraining load upon absorbing test solution as will be described.

The Centrifuge Retention Capacity (CRC) Test measures the ability of the superabsorbent composition to retain liquid therein after being saturated and subjected to centrifugation under controlled conditions. The resultant retention capacity is stated as grams of liquid retained per gram weight of the sample (g/g).

The superabsorbent polymer compositions according to the present invention can be employed in many products including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

The preparation of laminates in the broadest sense, and of extruded and coextruded, wet- and dry-bonded, as well as subsequently bonded structures, are possible as further preparation processes. A combination of these possible processes with one another is also possible.

The superabsorbent polymer compositions according to the invention may also be employed in absorbent articles that are suitable for further uses. In particular, the superabsorbent polymer compositions of this invention can be used in absorbent compositions for absorbents for water or aqueous liquids, desirably in constructions for absorption of body fluids, in foamed and non-foamed sheet-like structures, in packaging materials, in constructions for plant growing, as soil improvement agents, or as active compound carriers. For this, they are processed into a web by mixing with paper or fluff or synthetic fibers or by distributing the superabsorbent polymer composition particles between substrates of paper, fluff, or non-woven textiles, or by processing into carrier materials. They are further suited for use in absorbent compositions such as wound dressings, packaging, agricultural absorbents, food trays and pads, and the like.

The superabsorbent polymer compositions according to the invention show a significant improvement in permeability, i.e. an improvement in the transportation of liquid in the swollen state, while maintaining high absorption and retention capacity, as compared to known superabsorbent polymer compositions.

The present invention may be better understood with reference to the following examples.

Test Procedures

Free-Swell Gel Bed Permeability Test (FSGBP)

Figure 2:
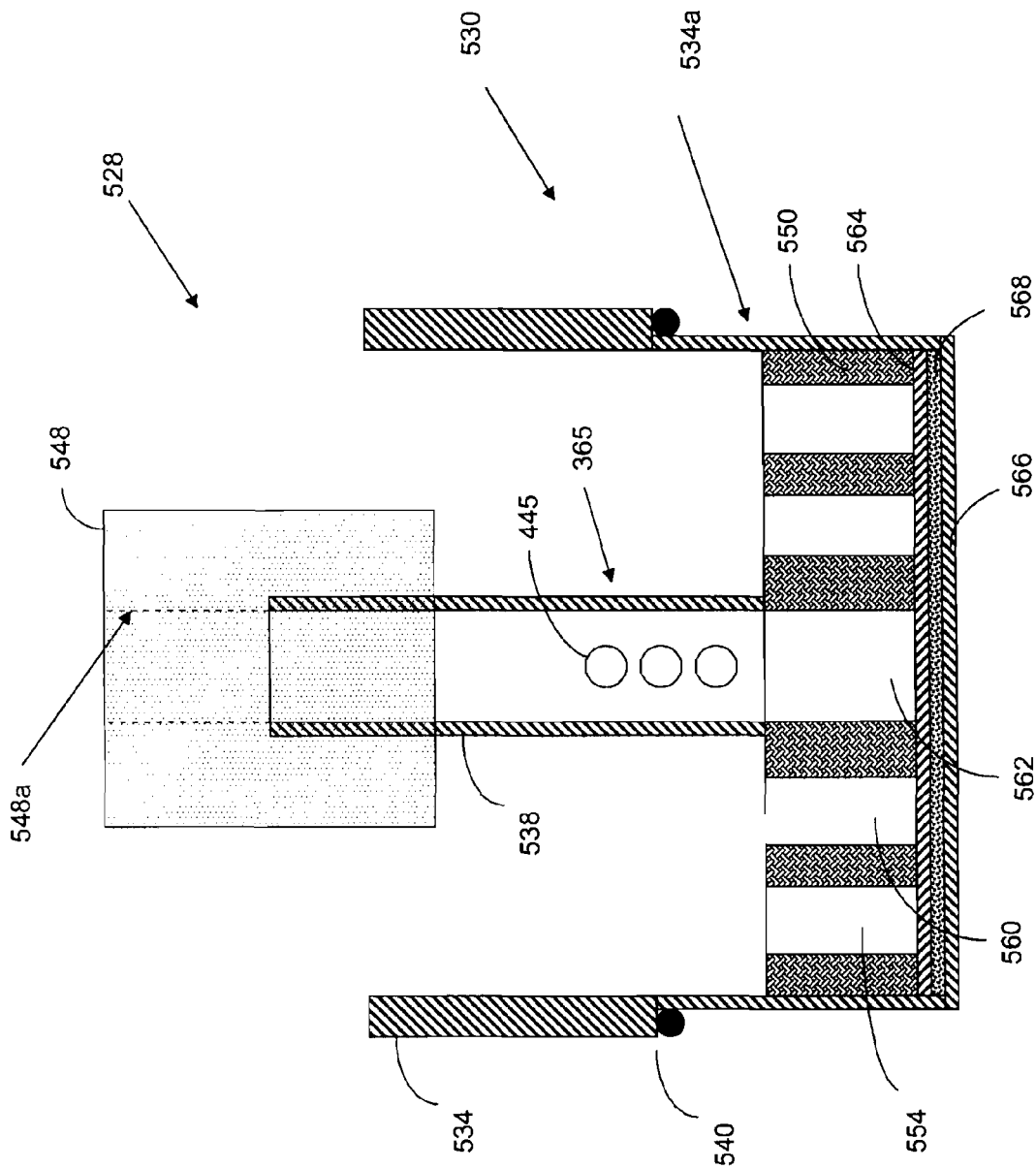
FIG. 2 is a cross-sectional side view of a cylinder/cup assembly employed in the Free Swell Gel Bed Permeability Test apparatus shown in FIG. 1.
Figure 3:
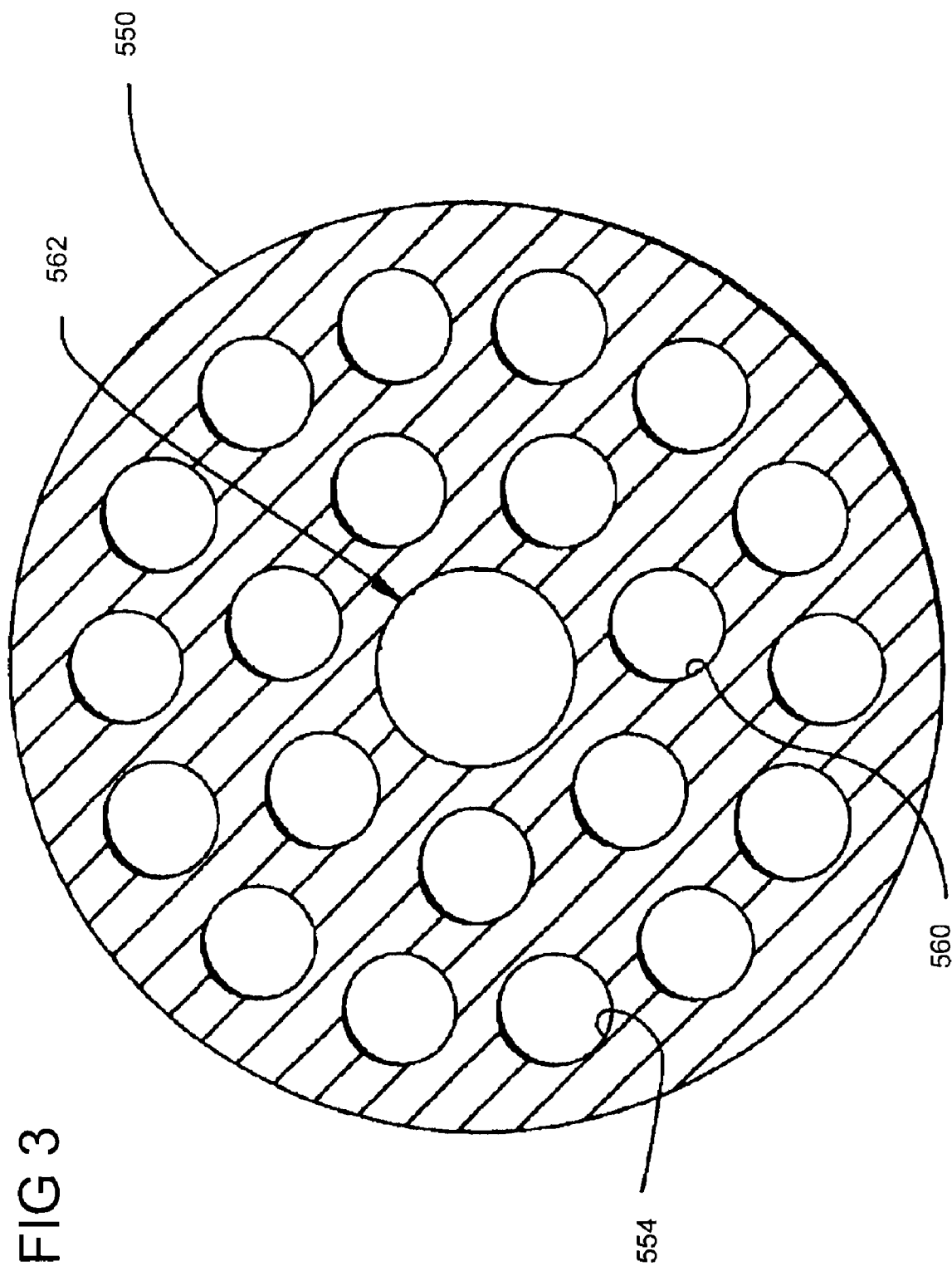
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2 and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm²), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm² (2.07 kPa), over a sample area of about 28.27 cm².

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The superabsorbent polymer particles can be prescreened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will prevent liquid in the sample container from being released onto a flat surface due to surface tension. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in cm² is obtained by the following equation: $K=[Q*H*\mu]/[A*\rho*P]$, where K=Permeability (cm²), Q=flow rate (g/sec), H=height of swollen sample (cm), $\mu$=liquid viscosity (poise) (approximately one centipoise for the test solution used with this Test), A=cross-sectional area for liquid flow (28.27 cm² for the sample container used with this Test), $\rho$=liquid density (g/cm³) (approximately one g/cm³, for the test solution used with this Test) and P=hydrostatic pressure (dynes/cm²) (normally approximately 7,797 dynes/cm²). The hydrostatic pressure is calculated from $P=\rho*g*h$, where $\rho$=liquid density (g/cm$^3$), g=gravitational acceleration, nominally 981 cm/sec$^2$, and h=fluid height, e.g., 7.95 cm for the Gel Bed Permeability Test described herein.

A minimum of two samples is tested and the results are averaged to determine the gel bed permeability of the sample.

Water Content

The amount of water content, measured as "% moisture," can be measured as follows: 1) Weigh 4.5-5.5 grams of superabsorbent polymer composition (SAP) accurately in a pre-weighed aluminum weighing pan; 2) place the SAP and pan into a standard lab oven preheated to 150° C. for 30 minutes; 3) remove and re-weigh the pan and contents; and 4) calculate the percent moisture using the following formula:

% Moisture={((pan wt+initial SAP wt)−(dried SAP & pan wt))*100}/dried SAP wt

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles that are pre-screened through a U.S. standard 30-mesh screen and retained on a U.S. standard 50-mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at about 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 290 g force with a variance from about 280 to about 300 g force), for 3 minutes. G force is defined as an unit of inertial force on a body that is subjected to rapid accelera-tion or gravity, equal to 32 ft/sec$^2$ at sea level. The bags are removed and weighed, with the empty bags (controls) being weighed first, followed by the bags containing the superabsorbent polymer composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$\frac{\text{sample/bag after centrifuge} - \text{empty bag after centrifuge} - \text{dry sample weight}}{\text{dry sample weight}}$$

The three samples are tested, and the results are averaged to determine the Centrifuge Retention Capacity (CRC) of the superabsorbent polymer composition.

Absorbency Under Load Test (AUL0.9 psi) The Absorbency Under Load (AUL) Test measures the ability of the superabsorbent polymer composition particles to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9" (22.9 cm×22.9 cm), with a depth of 0.5 to 1" (1.3 cm to 2.5 cm) is commonly used for this test method.

A 12.5 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 12.5 cm diameter filter paper circles.

A supply of saline (0.9% sodium chloride in distilled water, by weight).

Figure 4:
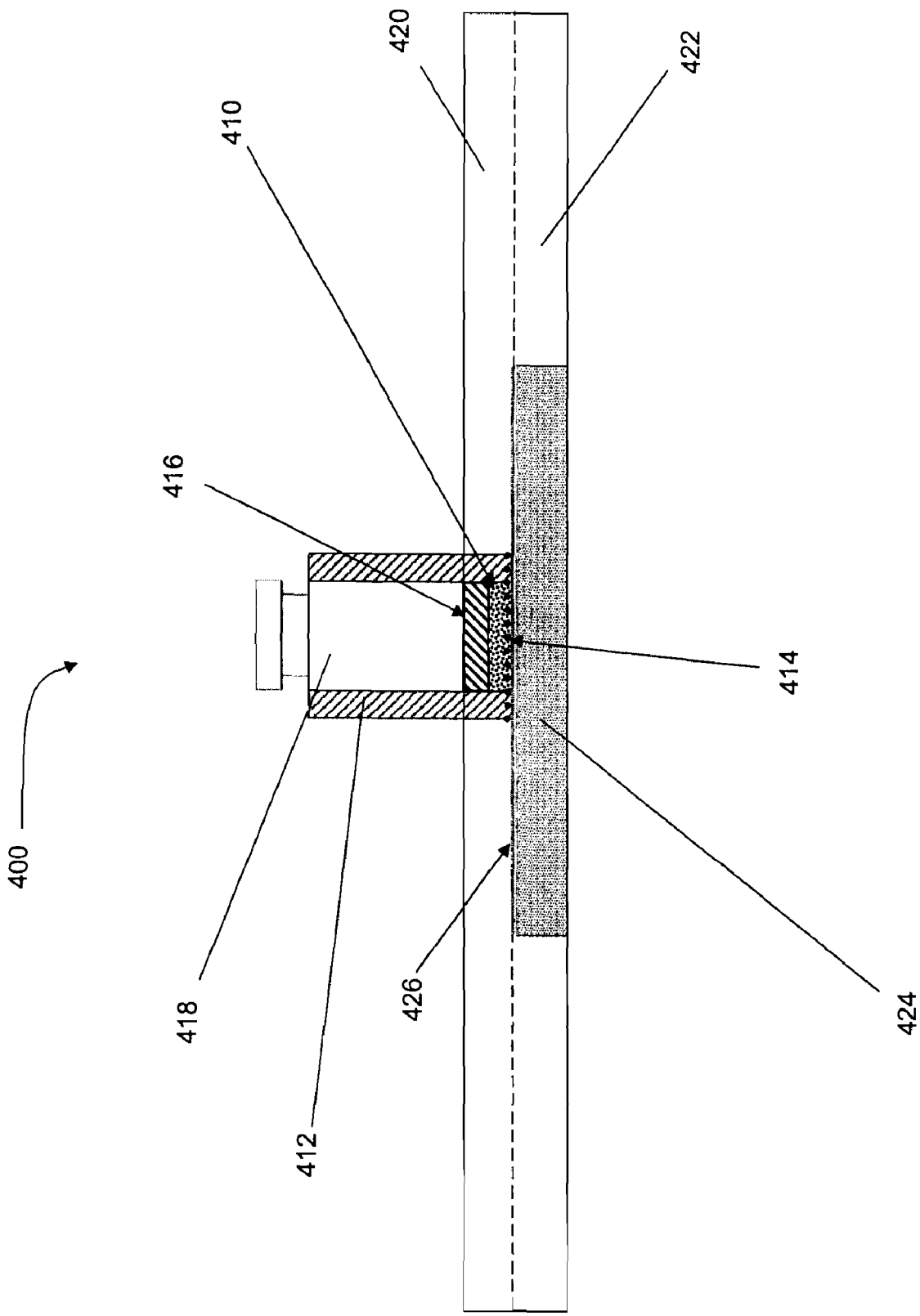
FIG. 4 is a side view of the test apparatus employed for the Absorbency Under Load Test.

Referring to FIG. 4, the cylinder 412 of the AUL assembly 400 used to contain the superabsorbent polymer composition particles 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard

30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition particles in the bottom of the cylinder is recorded as 'SA,' for use in the AUL calculation described below. Care is taken to be sure no superabsorbent polymer particles cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the superabsorbent polymer composition particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9\ psi) = (B - A)/SA$$

wherein

A=Weight of AUL Unit with dry SAP

B=Weight of AUL Unit with SAP after 60 minutes absorption

SA=Actual SAP weight

A minimum of two tests is performed and the results are averaged to determine the AUL value under 0.9 psi load. The samples are tested at about 23° C. and about 50% relative humidity.

EXAMPLES

The following examples and preproducts for the examples are provided to illustrate the invention and do not limit the scope of the claims. Unless otherwise stated all parts, and percentages are by weight.

Preproduct Fines

Into a polyethylene vessel equipped with an agitator and cooling coils was added, 25.0 kg of 50% NaOH to 37 kg of distilled water and cooled to 20° C. 9.6 kg of glacial acrylic acid was then added to the caustic solution and the solution again cooled to 20° C. 47.8 g of polyethylene glycol monoallylether acrylate, 47.8 g of ethoxylated trimethylol propane triacrylate SARTOMER® 454 product, and 19.2 kg of glacial acrylic acid were added to the first solution, followed by cooling to 4-6° C. Nitrogen was bubbled through the monomer solution for about 10 minutes. The monomer solution was then discharged in 7.7 kg batches into rectangular trays. To each batch 80 g of 1% by weight of $H_2O_2$ aqueous solution, 120 g of 2 wt % aqueous sodium persulfate solution, and 72 g of 0.5 wt % aqueous sodium erythorbate solution was added homogeneously into the monomer solution stream by injection of the sodium erythorbate solution into the stream of the monomer solution being conveyed from the monomer tank into a tray. The initiated monomer was allowed to polymerize for 20 minutes prior to grinding and drying at 175° C. The product was sieved with an Minox MTS 600DS3V to remove particles of remove particles greater than 850 microns and smaller than 150 microns. The particles that are smaller than 150 microns are Preproduct Fines.

Preproduct A

Into a polyethylene vessel equipped with an agitator and cooling coils was added, 25.0 kg of 50% NaOH to 37 kg of distilled water and cooled to 20° C. 9.6 kg of glacial acrylic acid was then added to the caustic solution and the solution again cooled to 20° C. 47.8 g of polyethylene glycol monoallylether acrylate, 47.8 g of ethoxylated trimethylol propane triacrylate SARTOMER® 454 product, and 19.2 kg of glacial acrylic acid were added to the first solution, followed by cooling to 4-6° C. Nitrogen was bubbled through the monomer solution for about 10 minutes, followed by the addition of 1.88 kg of Preproduct Fines. The monomer solution was then discharged in 7.7 kg batches into rectangular trays. To each batch 80 g of 1% by weight of $H_2O_2$ aqueous solution, 120 g of 2 wt % aqueous sodium persulfate solution, and 72 g of 0.5 wt % aqueous sodium erythorbate solution was added homogeneously into the monomer solution stream by injection of the sodium erythorbate solution into the stream of the monomer solution being conveyed from the monomer tank into a tray. The initiated monomer was allowed to polymerize for 20 minutes. The resulting gel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with an Minox MTS 600DS3V to remove particles greater than 850 μm and smaller than 150 μm.

Preproduct $AlPO_4$ Coating Slurry 1269 g of aluminum sulfate tetradecahydrate were dissolved in 1500 g deionized water having a temperature of about 85° C. to about 95° C. 860 g of trisodium phosphate was dissolved in 1200 g of hot deionized water. The aluminum sulfate solution is then rapidly poured into the trisodium phosphate solution. The resulting slurry was rapidly blended with 10 g PLURONIC® 25R2 surfactant which is available from BASF Corporation, Mount Olive, N.J., and sufficient 50% NaOH was added to bring the pH to neutral (pH of 7). 1413 g of pure ethylene carbonate was added to the solution to bring the net weight to 6.14 kg. The liquid slurry was filtered through a 100 mesh screen to remove any large particles prior to spraying onto Preproduct A.

$AlPO_4$ Presscake 1269 g of aluminum sulfate tetradecahydrate were dissolved in 1500 g hot deionized water. 860 g of trisodium phosphate was dissolved in 1200 g of hot deionized water having a temperature of from about 85° C. to about 95° C. The aluminum sulfate solution is then rapidly poured into the trisodium phosphate solution. The resulting slurry was rapidly blended with 10 g PLURONIC® 25R2 surfactant, and sufficient 50% NaOH was added to bring the pH to neutral (pH of 7). After precipitation of the $AlPO_4$, the suspension was filtered in a Büchner funnel and the resulting cake was washed with 3 500 mL additions of DI water. The presscake was measured as 20 wt % solids by oven drying.

Titanium Borate Presscake 200 g of disodium tetraborate was dissolved in 800 ml of hot deionized water. The water is in the temperature range of about 85° C. to about 95° C. 150 g of 45% titanium III sulfate was added to the above solution to form a dark slurry. 35% $H_2O_2$ was added drop-wise to the slurry until a homogenous yellow suspension resulted. The product was filtered in a Büchner funnel, and the cake was washed with deionized water. Solids were determined to be 19.8% by oven drying.

Comparative Examples 1 & 2 and Examples 1-7

Preproduct A was coated with 1 wt % ethylene carbonate and 4 wt % water using a 20 wt % aqueous solution. The coated Preproduct A was fed at a rate of 60-70 grams/minute into a continuous paddle reactor with a peak temperature of 215° C. and a residence time of about 50 minutes to accomplish surface crosslinking of the particulate polymer. The surface crosslinked particulate material was then post treated with the Surface Treatment set forth in Table 1.

TABLE 1

Comparative Examples 1 & 2 and Examples 1-7

| | Surface Treatments[1] | CRC g/g | Free swell (0 psi) GBP, Darcy | AUL(0.9 psi) |
|---|---|---|---|---|
| Comparative Example 1 | 5 wt % of a 1.6 wt % aqueous solution of PEG 8000 | 34.7 | 3 | 16.4 |
| Comparative Example 2 | 5 wt % water and then 0.5 wt % Sipernat ® 22S silica | 34.8 | 7 | 14.4 |
| Example 1 | 5.5 wt % of a 9.09 wt % $AlPO_4$ slurry (prepared from 2.5 parts $AlPO_4$ press cake and 3 parts water) to deliver 0.5% $AlPO_4$ and 5% water | 35.1 | 19 | 17.8 |
| Example 2 | 5.25 wt % of a 4.76 wt % $AlPO_4$ slurry (prepared from 1.25 parts $AlPO_4$ press cake and 4.25 parts water) to deliver 0.25 wt % $AlPO_4$ and 5 wt % water | 34.8 | 19 | 18.4 |
| Example 3 | 5.025 wt % of a 0.498 wt % $AlPO_4$ slurry (prepared from 0.125 parts $AlPO_4$ press cake, 2.5 parts 10% aqueous Lupamin ® 9095, and 2.4 parts water) to deliver 0.025 wt % $AlPO_4$, 0.25 wt % Lupamin ® 9095, and 4.75 wt % water | 35.5 | 17 | 16 |
| Example 4 | 5.25 wt % of a 4.76 wt % $AlPO_4$ slurry (prepared from 1.25 parts $AlPO_4$ press cake, 2.5 parts 10% aqueous Lupamin ® 9095, and 1.75 parts water) to deliver 0.25 wt % $AlPO_4$, 0.25 wt % Lupamin ® 9095, and 4.75 wt % water | 34.8 | 22 | 17.3 |
| Example 5 | 5.5 wt % 9.09 wt % TiBO slurry (prepared from 2.52 parts TiBO press cake and 2.97 parts water) to deliver 0.5% TiBO and 5% water | 35.1 | 24 | 16 |
| Example 6 | 5.25 wt % of a 4.76 wt % TiBO slurry (prepared from 1.26 parts TiBO press cake and 4.24 parts water) to deliver 0.25 wt % TiBO and 5 wt % water | 35.1 | 19 | 18 |
| Example 7 | 5.025 wt % of a 0.498 wt % TiBO slurry (prepared from 0.126 parts TiBO press cake, 2.5 parts 10% aqueous Lupamin ® 9095, and 2.4 parts water) to deliver 0.025 wt % TiBO, 0.25 wt % Lupamin ® 9095, and 4.75 wt % water | 35 | 13 | 15.5 |

[1]Post-treatment component added in combination with 5% wt water of preproduct.
2. Lupamin ® 9095 aqueous solution of polyvinyl amine Example 8

A blend of 2.5 parts of AlPO presscake, 1 part ethylene carbonate and 2 part water was prepared. The blend is sprayed onto 100 parts of Preproduct A with an air atomizer nozzle. The coated Preproduct A was fed at a rate of 60-70 grams/minute into a continuous paddle reactor with a peak temperature of 215° C. and a residence time of about 50 minutes to accomplish surface crosslinking of the particulate polymer. The surface crosslinked particulate material was then post treated with 2 wt % of a 10 wt % LUPAMIN® 9095 aqueous solution. The properties of Example 8 are CRC of 34.38 g/g; Free swell (0 psi) GBP, 51.0 Darcy; and AUL(0.9 psi) of 16.2.

Preproduct B

In an insulated, flat-bottomed reaction vessel, 1866.7 g of 50 wt % NaOH was added to 3090.26 g of distilled water and cooled to 25° C. 800 g of acrylic acid was then added to the caustic solution and the solution again cooled to 25° C. A second solution of 1600 g of acrylic acid containing 120 g of 50% by weight methoxypolyethyleneglycol monomethacrylate in acrylic acid and 14.4 g of ethoxylated trimethylolpropanetriacrylate was then added to the first solution, followed by cooling to 5° C., all while stirring. The monomer solution was then polymerized with a mixture of 100 ppm hydrogen peroxide, 200 ppm azo-bis-(2-amidino-propene)dihydrochloride, 200 ppm sodium persulfate, and 40 ppm ascorbic acid (all aqueous solutions) under adiabatic conditions and held near the maximum temperature ($T_{max}$) for 25 minutes. The resulting gel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with an Minox MTS 600DS3V to remove particles greater than 850 μm and smaller than 150 μm.

Example 9

Preproduct B was coated in an Anvil MIX9180 mixer with 1% ethylene carbonate, 4% water, 0.5% Preproduct $AlPO_4$ Slurry as described above, 350 ppm Chemcor 43G40SP (available from Chemcor Corporation, Chester N.Y.) maleated polypropylene, and 0.2% SIPERNAT® 22S silica based on the dry superabsorbent polymer composition weight. The coated superabsorbent polymer was heat treated to about 205° C. for about 45-50 minutes residence time in order to effectuate the surface crosslinking of the polymer particles.

After surface crosslinking the resulting particles were cooled to room temperature and then were post-treated by spraying the particles with a 2 wt % of a solution prepared from 5 parts of LUPAMIN® 9095 polyvinyl amine solution and 95 parts water in a kitchen type mixer with a wire whisk. The resultant product was allowed to equilibrate for at least 2 hours, and then sieved through U.S. standard #20 mesh screen and retained on U.S. standard #100 mesh screen.

TABLE 2

Example 9

| Example | Metal Compound | Polymeric Coating | CRC g/g | Free swell (0 psi) GBP, Darcy |
|---|---|---|---|---|
| 9 | 0.5% $AlPO_4$ | 350 ppm MPP[2] 2 wt % of 5 wt % LUPAMIN 9095[1] | 33.1 | 42.13 |

[1]LUPAMIN ® 9095 polyvinyl amine solution
[2]Meleated Polypropylene

In addition, the foregoing example was sieved using a RO-TAP® Mechanical Sieve Shaker Model B available from W. S. Tyler, Inc., Mentor Ohio and found to have the following particle size distribution as set forth in Table 3.

TABLE 3

Example 9 Particle Size Distribution

| Particle Size | Average % |
|---|---|
| % on 20 mesh (>850 μm) | 0.22 |
| % on 30 mesh (600-850 μm) | 20.79 |
| % on 50 mesh (300-600 μm) | 63.35 |
| % on 170 mesh (45-90 μm) | 15.6 |
| % on 325 mesh (45-90 μm) | 0.04 |
| % on 325 mesh (<45 μm) | 0 |

Example 10

Preproduct B was continuously coated in a Shugi mixer with 3% by weight of preproduct of a 33% aqueous EC solution, 2.5% by weight of preproduct of a 20% aluminum phosphate slurry, and 0.2% by weight of preproduct of SIPERNAT® S22S. The aluminum phosphate slurry was blended with Chemcor 43G40SP meleated polypropylene (MPP) to deliver 350 ppm MPP in the aluminum phosphate spray. Coated Preproduct B was then fed into a continuous paddle reactor for a residence time of about 30 minutes and a peak superabsorbent temperature of about 199° C. Surface-crosslinked superabsorbent polymer particles were then cooled and post-treated with 2% of a solution prepared from 5 parts LUPAMIN® polyvinyl amine solution and 95 parts water in an Anvil Model Number MIX9180 kitchen type mixer with a wire whisk. After post-treatment, superabsorbent polymer composition particles were allowed to stand for at least 2 hours prior to sieving through a U.S. standard #20 mesh and retained on U.S. standard #100 mesh screen. Example 10 superabsorbent polymer composition particles properties appear in Table 4.

TABLE 4

Example 10

| Example | CRC g/g | 0.0 GBP, Darcy | AUL(0.9 psi) |
|---|---|---|---|
| 10 | 33.2 | 47 | 16.6 |

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed:
1. A high-capacity superabsorbent polymer composition comprising a superabsorbent polymer comprising:
   a) from about 55% to about 99.9% by weight of polymerizable unsaturated acid group containing monomer, based on the superabsorbent polymer; and
   b) from about 0.001% to about 5% by weight of internal crosslinking agent based on the polymerizable unsaturated acid group containing monomer; wherein the superabsorbent polymer has a degree of neutralization of greater than about 25%; wherein elements a) and b) are polymerized and prepared into superabsorbent polymer particles and further comprising the following surface additives to form surface treated superabsorbent polymer particles
      i) from about 0.001% to about 5% by weight of surface crosslinking agent based on the superabsorbent polymer composition;
      ii) from about 0.01% to about 2% by weight of a water-insoluble inorganic metal compound, based on the superabsorbent polymer composition wherein said water-insoluble inorganic metal compound is selected from a calcium phosphate, titanium phos- phate, aluminum phosphate, iron phosphate, titanium borate, aluminum borate, iron borate magnesium borate, manganese borate, or calcium borate;

iii) from about 0.01% to about 0.5% cationic polymer based on the superabsorbent polymer composition; and iv) from about 0.01% to about 0.5% of a thermoplastic polymer that is selected from polyolefin, polyethylene, linear low density polyethylene, ethylene acrylic acid copolymer, styrene copolymers, ethylene alkyl methacrylate copolymer, polypropylene, maleated polypropylene, ethylene vinyl acetate copolymer, polyamide, polyester, blends thereof, or copolymers thereof.

2. The high-capacity superabsorbent polymer composition according to claim 1 wherein the superabsorbent polymer composition exhibits a centrifuge retention capacity as measured by the Centrifuge Retention Capacity Test of at least about 30 g/g and a free swell gel bed permeability of at least about 10 Darcy as measured by the Free Swell Gel Bed Permeability Test.

3. The high-capacity superabsorbent polymer composition according to claim 1 wherein the particles of the water-insoluble inorganic metal compound have a mass median particle size of less than 2 μm.

4. The high-capacity superabsorbent polymer composition of claim 1 wherein the cationic polymer is a polyvinylamine.

5. The high-capacity superabsorbent polymer composition of claim 1 having a centrifuge retention capacity of at least about 32 g/g as measured by the Centrifuge Retention Capacity Test, and a free swell gel bed permeability of at least about 20 Darcy as measured by the Free Swell Gel Bed Permeability Test.

6. The high-capacity superabsorbent polymer composition of claim 1 wherein the thermoplastic polymer is a maleated polypropylene.

7. The high-capacity superabsorbent polymer composition of claim 1 having a centrifuge retention capacity from about 32 g/g to about 40 g/g as measured by the Centrifuge Retention Capacity Test, and a free swell gel bed permeability of at least about 40 Darcy as measured by the Free Swell Gel Bed Permeability Test.

8. The high-capacity superabsorbent polymer composition of claim 1 wherein at least about 40% by weight of the surface treated superabsorbent polymer particles have a particle size from about 300 μm to about 600 μm.

9. The high-capacity superabsorbent polymer composition of claim 1 wherein at least about 50% by weight of the surface treated superabsorbent polymer particles have a particle size from about 300 μm to about 600 μm.

10. The high-capacity superabsorbent polymer composition according to claim 1 wherein the surface treated superabsorbent polymer particles are heat-treated.

11. The high-capacity superabsorbent polymer composition according to claim 1 wherein the particles of the water-insoluble inorganic metal compound have a mass median particle size of less than about 1 μm.

* * * * *

UNITED STATES PATENT AND TRADEMARK OFFICE
CERTIFICATE OF CORRECTION

| | | |
|---|---|---|
| PATENT NO. | : 8,236,884 B2 | Page 1 of 1 |
| APPLICATION NO. | : 11/690611 | |
| DATED | : August 7, 2012 | |
| INVENTOR(S) | : Scott J. Smith, Stan McIntosh and David L. Bergman, Jr. | |

It is certified that error appears in the above-identified patent and that said Letters Patent is hereby corrected as shown below:

Title Page, correct the Inventors data in item (75) with the following paragraph:

-- Inventors: Scott J. Smith, Greensboro, NC (US); Stan McIntosh, Greensboro, NC (US); David L. Bergman, Jr., Greensboro, NC (US) --.

Signed and Sealed this
Sixteenth Day of October, 2012

David J. Kappos
*Director of the United States Patent and Trademark Office*